(12) United States Patent
Hillion et al.

(10) Patent No.: US 7,420,073 B2
(45) Date of Patent: Sep. 2, 2008

(54) PROCESS FOR THE ALCOHOLYSIS OF ACID OILS OF VEGETABLE OR ANIMAL ORIGIN

(75) Inventors: Gérard Hillion, Herblay (FR); Dominique Le Pennec, Orgerus (FR)

(73) Assignee: Institut Francais du Petrole, Rueil Malmaison Cedex (FR)

(*) Notice: Subject to any disclaimer, the term of this patent is extended or adjusted under 35 U.S.C. 154(b) by 497 days.

(21) Appl. No.: 10/802,042

(22) Filed: Mar. 17, 2004

(65) Prior Publication Data

US 2005/0113588 A1 May 26, 2005

(30) Foreign Application Priority Data

Mar. 17, 2003 (FR) .................................. 03 03575

(51) Int. Cl.
*C07C 51/09* (2006.01)

(52) U.S. Cl. .................. 554/174; 554/167; 554/169

(58) Field of Classification Search .......... 554/174, 554/167, 169
See application file for complete search history.

(56) References Cited

U.S. PATENT DOCUMENTS

| 2,383,601 | A | * | 8/1945 | Keim ................... 554/167 |
| 5,908,946 | A | | 6/1999 | Stern et al. |
| 6,245,727 | B1 | * | 6/2001 | Gutsche et al. ........... 508/591 |
| 6,960,673 | B2 | * | 11/2005 | Brunner et al. .......... 554/174 |

FOREIGN PATENT DOCUMENTS

| EP | 0 924 185 | 6/1999 |
| WO | 93 01263 | 1/1993 |

* cited by examiner

*Primary Examiner*—Elvis O. Price
(74) *Attorney, Agent, or Firm*—Millen, White, Zelano, Branigan, P.C.

(57) ABSTRACT

A process that employs a heterogeneous catalyst comprising a zinc aluminate mixed oxide and having the following formula:

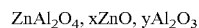

in which x and y each represent a number in the range 0 to 2, and in which the zinc aluminate is more particularly of the spinel type, makes it possible, by means of C1 to C5 monoalcohols, to:
- transesterify vegetable or animal oils having a natural free acidity, such as unrefined degummed rapeseed, soya, sunflower oils or exotic oils of the African oil, palm nut oil or coconut oil type, which are naturally rich in fatty acids;
- and simultaneously esterify their free acidity;

so as to use phospholipid free and/or degummed unrefined acid oil with an acid number in the range 0.5 to 20, for example 1 to 15 and preferably 2 to 12, to produce esters, for example methyl esters, for use as fuels.

12 Claims, No Drawings

PROCESS FOR THE ALCOHOLYSIS OF ACID OILS OF VEGETABLE OR ANIMAL ORIGIN

CROSS-REFERENCE TO RELATED APPLICATIONS

This application is related to Applicants' concurrently filed application Ser. No. 10/801,543, entitled "Process For Preparation Of A Catalyst Based On Zinc Aluminate And The Catalyst That is Obtained".

The present invention relates to the alcoholysis of acid oils of vegetable or animal origin.

More particularly, it pertains to a process consisting of using a starting oil of vegetable or animal origin having a free fatty acidity, expressed by its acid number (AN), transesterifying it with a C1 to C6 monoalcohol, simultaneously esterifying the free acidity using a C1 to C5 mono-alcohol to produce esters of C1 to C6 monoalcohols and C6 to C26 fatty acids.

In the present invention, the acid number (AN) is in the range 0.5 to 20, for example 1 to 15 and preferably 2 to 12.

The AN is expressed as the number of mg of KOH necessary to neutralize 1 g of product. The acidity of an oil or fatty substance can also be expressed as the weight % of fatty acid. It is generally the fatty acid which is in the majority in the oil which is taken into account; for example, for rapeseed oil, the acidity is expressed as the % by weight of oleic acid.

In contrast to processes for esterifying vegetable oils using homogeneous basic catalysis, it has surprisingly been discovered that by using, for example, a fatty substance having an acid number in the range 0.5 to 20, for example 1 to 15 and more particularly 2 to 12, esterification of the fatty acids can be carried out simultaneously with transesterification of the oil by methanol using a fixed bed heterogeneous catalyst under certain conditions. This reaction can encompass higher monoalcohols such as ethanol, 1-propanol, isopropanol, 1-butanol, isobutanol, 1-pentanol or hexanol-1.

This catalytic process uses two reaction steps and can simultaneously transform triglycerides and fatty acids to methyl esters, for example in the context of the production of esters for fuel use.

It is also possible to use the catalytic properties of said system to transesterify the monoalcohol esters obtained by heavy alcohols such as 2-ethylhexanol or by polyols such as 1,2-propylene glycol, 1,3-propylene glycol, glycerol, neopentyl glycol, trimethylol-propane, pentaerythritol, etc. These conditions employ atmospheric pressure to encourage the monoalcohol to leave the reaction medium, substantially displacing the reaction equilibrium.

Under conventional processes for producing esters using basic catalysis (hydroxides or alkaline alcoholates), the acid number of the oils used is usually less than 1. For values of more than 1, homogeneous basic catalysis can be unacceptable, as the quantity of catalyst to be used then becomes directly proportional to the acid number of the oil used. This leads to the formation of a large quantity of soaps, further reducing the overall yield of the operation, not to mention the difficult and expensive steps for eliminating the soaps produced.

As an example, to carry out methanolysis of a neutralized vegetable or animal oil with an acid number of 0.5 or less, the quantity of sodium methylate required to obtain optimum conversion to methyl esters is of the order of 70 moles of sodium equivalent/tonne of oil employed. In the case of an oil with an AN of 10, the quantity of alcoholate to be used would be increased by 180 moles of sodium equivalent and would represent a supplemental quantity of soaps of the order of 55 kg/tonne or oil. In addition to the extra cost of catalyst, eliminating such a quantity of soap is difficult and expensive, causing a reduction in yield of the order of 5.6 weight %.

For this reason, it is vital to refine the oil to reduce the free acidity either by chemical treatment or by a physical treatment depending on the initial acidity of the oil employed.

The present invention concerns the use of all unrefined vegetable oils free of their phospholipids or gums, recovered oils such as those used for frying, and animal fats with an acid number (AN) in the range 0.5 to 20.

Examples of conventional refining processes that can be cited are neutralizing distillation applicable to dense oils such as African oil, palm nut oil and coconut oil, these containing little or no phospholipids; they consist of entrainment in steam under high vacuum for example at a temperature of 235° C.

For other types of oils such as soya, rapeseed, sunflower, corn, peanut, cotton, shea, crambe, safflower, castor etc., chemical refining is carried out after a degumming step consisting of rendering the phospholipids insoluble by hydration.

Those hydrated phospholipids can be eliminated
separately prior to the neutralization step, for example in the case of soya where those products (the phospholipids), rich in lecithin, are upgraded in the food industry for use as emulsifying agents,
or at the same time as the soaps after the neutralization step using soda lye.

Separating the soaps resulting from the neutralization step using a soda lye solution is usually carried out by centrifuging. The sodium soaps obtained are also termed "soapstocks" or neutralization paste. They represent the vast majority of the losses of fatty materials in oil refining. The degree of impregnation of oil in the soapstocks varies from 15% to 100%, and can be expressed as the neutralization coefficient, which in that case is in the range 1.15 to 2.

This loss of fatty material is proportional to the acid number of the oil and can be as high as 2% to 4% by weight of the oil employed for the usual European oils, such as rapeseed oil or sunflower oil.

That fraction constituting the soapstocks is upgraded to a small extent into an acid oil obtained following a neutralization step using a strong acid, termed soapstock breaking.

Some "biodiesel" production processes which use acid oils such as African oil include a preliminary step which consists of esterifying the free fatty acids with a C1 to C5 monoalcohol in the presence of a catalyst usually with a highly acidic nature, such as sulfuric acid (U.S. Pat. No. 2,383,601) or hydrochloric acid, or a sulfonic acid which may be soluble or supported in the form of recyclable ion exchange resins (French patent FR-B1-2 577 938).

The reduction in acidity allows the subsequent step to be carried out, which consists of transesterification by basic catalysis (alkali alcoholate) of all of the oil.

Such processes, which usually employ methanol, require fairly long residence times and large quantities of alcohol. Said excess alcohol is necessary to displace the equilibrium by eliminating the water formed during the esterification reaction. It involves physical entrainment of the water, as the methanol/water mixture does not form an azeotrope. The recovered methanol/water mixture must in that case be rectified to recycle the large excess of alcohol.

A further solution envisaged using strongly acidic oils, in the particular case of palm oils which can have ANs of more than 30, is to reduce the palmitic acidity by carrying out a step for glycerolysis of free fatty acids, which consists of esterification of the free fatty acids with a small quantity of glycerol, by using the same catalyst as that described in the invention. That process is particularly suitable for the production of fuel esters, as described in the Applicant's U.S. Pat. No. 5,908,946 which also describes the mode of preparing the catalyst and the catalysis conditions.

Thus, the aim of the invention is to replace certain treatments associated with stages in refining vegetable oil, which normally reduce their acid number to low values, usually to less than 1, which involves using, in the process of the invention, a non deacidified vegetable oil having a final acid number which is preferably in the range 0.5 to 20, for example 1 to 15 and preferably 2 to 12, which derives from pressure and/or extraction treatment and which has undergone a degumming step to obtain a residual phosphorous content of less than 10 ppm, followed by a drying step to obtain a residual water content of less than 500 ppm.

The invention provides a process for the alcoholysis of acid oils of vegetable or animal origin which, with C1 to C5 mono alcohols, can transesterify vegetable or animal oils with a natural free acidity and simultaneously esterify their free acidity, characterized in that it comprises two catalysis steps in two reactors functioning with a heterogeneous fixed bed catalyst.

More particularly, the process of the invention can be characterized in that it comprises:

a catalytic reaction step a) in which an aliquot quantity of oil and monoalcohol are simultaneously introduced into a first reactor, pre-heated to a temperature in the range 180° C. to 210° C. and at an operating pressure in the range 40 to 60 bars (4 to 6 MPa);

a step b) in which the reaction mixture leaving the said catalysis reactor undergoes complete or partial evaporation of the excess monoalcohol, encouraging separation of the glycerol formed, which is recovered;

a step c) in which the ester mixture is introduced into a second reactor with the addition of the equivalent by weight of monoalcohol;

a step d) in which the mixture from step c) undergoes complete evaporation of the excess monoalcohol, then the residual glycerol formed is eliminated.

Preferably in the process of the invention, the two reactors are substantially identical in size and step c) is carried out under the catalysis conditions of the first catalysis step a).

Thus the process of the invention consists of working in two catalysis steps in two reactors of substantially identical sizes and which function with a heterogeneous fixed bed catalyst.

The heterogeneous catalyst generally comprises a zinc aluminate and has the following formula:

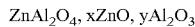

$ZnAl_2O_4, xZnO, yAl_2O_3$ in which x and y are in the range 0 to 2, the zinc aluminate more particularly having a spinel type structure.

Using two metering pumps, an aliquot of oil and monoalcohol are introduced into the first reactor, which is pre-heated to a temperature in the range 180° C. to 210° C. and at an operating pressure in the range 40 to 60 bars (4 to 6 MPa). At the outlet from the first catalysis, the reaction mixture undergoes complete or partial evaporation of the excess methanol, encouraging separation of the glycerol formed, which is recovered after a static decanting step.

This intermediate step for eliminating the glycerol can displace the reaction equilibrium to obtain, in the second reactor, maximum conversion to methyl esters.

To this end, the ester mixture obtained is introduced into a second reactor with addition of the equivalent weight of methanol. The catalysis conditions are identical to those recommended for the first catalysis step.

At the end of said second step, the mixture undergoes complete evaporation of the excess methanol, then the residual glycerol formed is eliminated.

The finished product, which is characterized by a mixture of fatty acid esters, satisfies current specifications regarding diesel engine fuel both as regards the methyl ester contents and the value of the final acid number.

The following non-limiting examples are given by way of illustration alone.

EXAMPLE 1

Methanol transesterification of a semi-refined rapeseed oil was carried out in a continuous reactor in the presence of a heterogeneous catalyst used in a fixed bed (the semi-refined rapeseed oil had not undergone the decolorization and deodorizing steps necessary for producing a food quality oil).

This consisted of passing, into a mono-tube reactor containing 70 ml of catalyst based on zinc aluminate extrudates, a 50/50 by weight mixture of oil and methanol introduced separately via two metering pumps. The corresponding volumes were 35 ml of oil and 40 ml of methanol/hour, corresponding to a residence time for the oil/methanol mixture on the catalyst of about 56 minutes.

The temperature was kept at 200° C. and the pressure stabilized between 50 and 60 bars (between 5 and 6 MPa).

After operating for 4 to 5 hours to obtain stabilized conversion, analysis of the reaction mixture by GPC (gel permeation chromatography) allowed the composition of the mixture, principally constituted by methyl esters, unconverted triglycerides, diglycerides, monoglycerides and free or partially esterified sterols, to be quantified.

The process was run for at least 72 hours to recover a sufficient quantity of products, namely about 2.5 liters of ester mixture, which would supply the same reactor to simulate a second catalysis step necessary to obtain better conversion to methyl esters.

All of the mixture recovered after 72 hours operation was evaporated completely in a rotary evaporator to eliminate the excess methanol, then it was freed of the glycerol formed during transesterification by static decanting at 50° C.

The mixture constituted by about 94.7% pure methyl esters was then re-introduced into the reactor with an equivalent quantity of methanol by weight, i.e. 50/50, under the same operating conditions, namely: a temperature of 200° C. and a pressure between 50 and 60 bars (between 5 and 6 MPa), and with respective flow rates of esters and methanol of 35 ml and 40 ml/hour.

The reaction mixture was completely evaporated then after decanting, the glycerol formed was separated and the ester mixture obtained was analyzed by GPC. The results are shown in Table 1.

TABLE 1

Composition of esters produced from semi-refined rapeseed oil

| Rapeseed oil AN = 0.5 max | TG | DG + sterols | MG | RME + fatty acids | AN |
|---|---|---|---|---|---|
| first catalysis step | 0.4 | 1.7 | 2.2 | 94.7 | 0.3 |
| second catalysis step | 0 | 0.75 | 0.5 | 98.75 | 0.2 |

TG: triglycerides (oil)
DG: diglycerides
MG: monoglycerides
RME: rapeseed methyl esters
AN: acid number

EXAMPLE 2

The operating procedure was that described in Example 1, however the nature of the rapeseed oil used differed by its acid number, which in this case was 11.

This oil was reconstituted from a weighed mixture of distilled oleic acid and semi-refined rapeseed oil, identical to that used in Example 1.

Three kilograms of said oil were produced as follows: a mixture of 165 g of distilled oleic acid and 2835 g of semi-refined rapeseed oil. The acid number of this mixture was determined using French standard NF ISO 660 and gave an AN of 11.

Two catalysis steps were carried out under the conditions given for Example 1.

The results are shown in Table 2.

TABLE 2

Composition of esters produced from acid oil

| Rapeseed oil AN = 11 | TG | DG + sterols | MG | RME + fatty acids | AN |
|---|---|---|---|---|---|
| first catalysis step | 4.10 | 4.90 | 4.20 | 86.80 | 1.6 |
| second catalysis step | 0.05 | 0.95 | 0.60 | 98.40 | 0.35 |

TG: triglycerides (oil)
DG: diglycerides
MG: monoglycerides
RME: rapeseed methyl esters
AN: acid number The water produced during the esterification reaction was primarily trapped in the glycerin phase. This water was also a catalysis inhibitor, as can be adjudged from Example 3.

EXAMPLE 3

A series of tests (5 tests) concerning the first catalysis step was carried out, varying the water content of the feed and using the operating procedure described in Example 1.

The semi-refined rapeseed oil had a maximum acid number AN of 0.5 and a water content of 400 ppm of water. The methanol contained the following quantities of water in succession: 500, 1500, 3000 and 6000 ppm.

Each test lasted 48 hours to guarantee good conversion stability. A reversal was carried out at the end of the test using dry methanol (500 ppm water).

The oil-methanol mixture was 50/50 by weight; thus, the different water contents in the feed were 450, 950, 1750 and 3250 ppm for the 4 tests respectively.

The results obtained are shown in Table 3.

TABLE 3

Influence of water content in feed (oil + methanol) on the composition of the esters produced

| Water content in feed (ppm) | TG | DG + sterols | MG | RME + fatty acids | AN |
|---|---|---|---|---|---|
| Test 1 | 450 | 0.4 | 1.7 | 2.2 | 94.7 | 0.12 |
| Test 2 | 950 | 1.4 | 2.7 | 3.0 | 92.9 | 0.17 |
| Test 3 | 1750 | 3.3 | 3.8 | 4.8 | 88.1 | 0.30 |
| Test 4 | 3250 | 4.6 | 5.5 | 5.2 | 84.7 | 0.68 |
| Test 5 | 450 | 0.5 | 1.7 | 2.3 | 94.5 | 0.12 |

TG: triglycerides (oil)
DG: diglycerides
MG: monoglycerides
RME: rapeseed methyl esters
AN: acid number It can be seen that the variation in the conversion to methyl esters was inversely proportional to the water content of the feed (oil+methanol).

Water acts as an inhibitor, but this action is labile as on returning (test 5) to the initial operating conditions (test 1) with 450 ppm of water in the feed, an identical methyl ester conversion was regained.

The esterification reaction generates water, and thus the water content of the feed will increase and become critical for conversion to methyl esters. Thus, operating conditions close to those of Example 3, which depend on the acid number of the oil employed, are rapidly obtained.

Analyzing the results of Table 2 concerning Example 1, in which a mixture with an acid number of 1.6 is obtained at the end of the first catalysis from an oil with an acid number of 11, the quantity of water generated corresponding to esterification of one equivalent of fatty acid can be calculated. In this case, of the order of 3000 ppm of water is calculated as being formed in the reaction mixture.

Comparing this result with those of Example 3 (Table 3), it can be seen that this is close to the conversion values obtained by adding equivalent quantities of water (Table 3-test 4).

This approach to the process of the invention fixes its limits and the skilled person can define a maximum acidity so as not to penalize the composition of the mixture of fatty acid esters resulting from the 2 catalysis steps.

To exceed these limits, multiplication of the catalysis steps would be a possible solution provided that operating costs remained competitive compared with operating conditions for reducing the acidity of acid oils as cited above with the example of esterification by methanol employing homogeneous catalysis via mineral sulfuric or hydrochloric type acids.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 03/03/575, filed Mar. 17, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

It is preferred to employ as the catalyst, a zinc aluminate prepared in accordance with the above recited cross-referenced application. In particular, the catalyst produced by that process exhibit improved crushing strengths.

The invention claimed is:

1. A process for the alcoholysis of a non-deacidified vegetable or animal oil having natural free acidity, comprising first catalytically reacting in the presence of a heterogeneous fixed bed catalyst comprising a zinc aluminate mixed oxide of the formula $ZnAl_2O_4$, $xZnO$, $yAl_2O_3$, in which x and y each represent a number in the range 0 to 2, said vegetable or animal oil with C1 to C5 monoalcohols in a first reactor, and second catalytically reacting in the presence of a heterogeneous fixed bed catalyst the ester mixture previously obtained, in a second reactor, transesterifying said vegetable or animal oils and simultaneously esterifying their free acidity.

2. A process for the alcoholysis of a non-deacidified vegetable or animal oil having natural free acidity according to claim 1, comprising:

(a) catalytically reacting said vegetable or animal oils in a first reactor with C1 to C5 mono-alcohols in the presence of the zinc aluminate mixed oxide catalyst, to esterify free acidity and transesterify the oils;

(b) treating the reaction product from the first catalytic reactor so as to completely or partially evaporate excess mono-alcohols and at least partially separating resultant glycerol; and (c) introducing resultant mixture of transesterified oils into a second reactor along with additional mono-alcohol, in the presence of a heterogeneous fixed bed catalyst, so as to increase the yield of resultant transesterified oils; and separating residual glycerol and mono-alcohols from the resultant transesterified oils.

3. A process according to claim 1, comprising:

a catalytic reaction a) simultaneously introducing an aliquot quantity of oil and the monoalcohol into said first reactor, pre-heated to a temperature in the range 180° C. to 210° C. and at an operating pressure in the range 4 to 6 MPa;

b) completely or partially evaporating a reaction mixture leaving the first catalysis reactor of the excess mono-, encouraging separation of the glycerol formed, which is recovered;

c) introducing the ester mixture into the second reactor with addition of the equivalent by weight of monoalcohol;

d) complete evaporation of the mixture from step c) undergoes complete evaporation of the excess monoalcohol, and eliminating residual glycerol formed.

4. A process according to claim 1, wherein the zinc aluminate of the catalyst has a spinel structure.

5. A process according to claim 2, wherein the two reactors are substantially identical in size and step c) is carried out under the catalysis conditions of the first catalysis step a).

6. A process according to claim 1, wherein the starting oil is unrefined, naturally fatty acid-rich degummed rapeseed, soya or sunflower oil.

7. A process according to claim 1, wherein the starting oil is naturally fatty acid-rich exotic African palm, palm nut oil or coconut oil.

8. A process according to 1, wherein an unrefined acid oil freed of its phospholipids and/or gums and with an acid number between 0.5 and 20 is used.

9. A process according to claim 8, wherein the acid number is between 1 and 15.

10. A process according to claim 8, wherein the acid number is between 2 and 12.

11. A process according to claim 9, wherein the oil results from pressure and/or extraction and has undergone degumming to obtain a residual phosphorous content of less than 10 ppm followed by drying to obtain a residual water content of less than 500 ppm.

12. A process according to claim 1, wherein the mono alcohol is methanol.

* * * * *